United States Patent [19]

Szablikowski et al.

[11] Patent Number: 5,585,471
[45] Date of Patent: Dec. 17, 1996

[54] METHOD FOR PREPARING A MIXTURE OF α- AND β-CHLOROETHYL-GLUCOPYRANOSE

[75] Inventors: Klaus Szablikowski; Martin Lohrie, both of Walsrode; Wolfgang Koch, Bomlitz; Reinhard Langer; Hans-Josef Buysch, both of Krefeld, all of Germany

[73] Assignee: Wolff Walsrode Aktiengesellschaft, Walsrode, Germany

[21] Appl. No.: 339,526

[22] Filed: Nov. 15, 1994

[30] Foreign Application Priority Data

Nov. 22, 1993 [DE] Germany ............... 43 39 698.4

[51] Int. Cl.$^6$ ........................................ C07H 1/00
[52] U.S. Cl. ............ 536/18.5; 536/1.1; 536/1 KW; 536/4.1; 536/18.4; 536/122
[58] Field of Search ................... 536/4.1, 17.3, 536/17.4, 17.9, 120, 18.4, 18.5, 1.1, 122

[56] References Cited

U.S. PATENT DOCUMENTS 4,663,448  5/1987  Chiu ........................... 536/111
4,719,272  1/1988  Tsai et al. ..................... 536/4.1

FOREIGN PATENT DOCUMENTS 0132046  1/1985  European Pat. Off. .
0362671  4/1990  European Pat. Off. .

OTHER PUBLICATIONS

L. Hough, et al., Recal. Trav. Chim. Pays–Bas, vol. 110, pp. 450–458 (1991).

*Primary Examiner*—James O. Wilson
*Attorney, Agent, or Firm*—Sprung Horn Kramer & Woods

[57] ABSTRACT

A method for preparing a chloroethylglucopyranose which comprises
  a) reacting glucose with from 2 to 10 times the molar amount of chloroethanol at from 100° to 130° C. in the absence of a catalyst, optionally removing water,
  b) further reacting the product of step (a) at 60° to 90° C. in the presence of an acidic catalyst for from 10 to 600 minutes and
  c) Separating therefrom the chloroethylglucopyranose.

5 Claims, No Drawings

METHOD FOR PREPARING A MIXTURE OF α- AND β-CHLOROETHYL-GLUCOPYRANOSE

The present invention provides a particularly mild method for preparing chloroethylglucopyranose by the Fischer synthesis having a high production output.

The simplest method for the synthesis of alkylpyranoses is the acid-catalysed conversion of the reducing sugars with the corresponding alcohols as reagent and solvent, with the elimination of water. Unlike the practice common as a rule in sugar chemistry, no costly auxiliary reagents are used here and consequently no unavoidable by-products which may cause problems are formed either.

The formal simple reaction scheme of the acetalation of the anomeric carbon atom in reducing $C_6$ sugars is not, as intensive investigations have shown, a representation of the processes actually taking place in the reaction mixture ("Chemistry of the o-glycosidic bond", A. F. Bochkov and G. E. Zaikov, Pergamon Press, Oxford 1979).

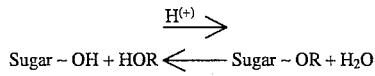

More accurately, a complex system of open-chain, furanoside and pyranoside sugar derivatives are formed in the solution. The composition of the mixture in equilibrium depends primarily on the sugar and almost always lies on the side of the pyranose.

Thus the equilibrium mixture of glucose in methanol at 35° C. contains 1.5% of furanosides and 98.5% of pyranosides.

However, under kineticall controll the furanoside structures are formed first. In connection with this, see "Chemistry of the o-glycosidic bond", A. F. Bochkov and G. E. Zaikov, Pergamon Press, Oxford 1979, pages 11–16 and R. J. Ferrier, Topics in Current Chemistry 14 389 (1970).

The reaction to the thermodynamically favoured pyranoses proceeds very slowly and leads to a product mixture of anomeric furanosides and pyranosides. Soluble acids and ion-exchange resins are described as catalysts, for example, by G. N. Bollenbach et al. in Methods in Carbohydrate Chemistry, Vol. 2, Academic Press, New York and London, 1963, page 228. The removal of the water formed in the reaction from the equilibrium system by means of zeolites is also known and is described by M. B. Kozikowski et al. in Roczniki Chemii, 47, 1899 (1973).

The prior art relating to the synthesis of chloroethylglucopyranose is described in Example 21 of U.S. Pat. No. 4,719,272. There 80 g of dextrose (0.5 mol) in 148 ml (2.2 mol) of chloroethanol together with 20 g of Dowex 50 W-X8 in the H+ form are stirred at 90° C. until the glucose has dissolved and then maintained at 60° C. for 16 hours.

According to prior scientific knowledge it may be assumed that the low temperatures and the long reaction time are necessary for the establishment of the pyranoside equilibrium. At higher temperatures sugars as a rule form coloured by-products, which are to be avoided.

Surprisingly, it has now been found that the synthesis of chloroethylglucopyranose can be performed considerably faster if the glucose is previously dissolved in chloroethanol in the absence of a catalyst at relatively higher temperatures, with water optionally being removed by distillation, in order then to complete the reaction by addition of the acidic ion exchanger at a lower temperature. By this means only very slightly discoloured material is obtained in a distinctly shorter time and using distinctly less catalyst.

The invention provides a method for preparing chloroethylglucopyranose which is characterised in that 1 mole of glucose is previously dissolved in from 2 to 10, preferably from 3 to 8, particularly preferably 4 to 6 moles of chloroethanol at 100° to 130° C., preferably 110° to 120° C., in the absence of additional catalysts, with water optionally being removed by distillation, and subsequently from 1 to 30, preferably from 2 to 20, particularly preferably 4 to 10% by weight of acidic catalyst, based on the glucose, is added at 60° to 90° C., preferably at 70° to 80° C. and stirring is continued for a further 10 to 600, preferably 20 to 300, particularly preferably 30 to 100 minutes.

The dissolution of the glucose does not last longer than 60 minutes. At 80° C., approximately 90% of the glucose has reacted 30 minutes after addition of the ion exchanger, approximately 95% after 90 minutes and approximately 97% after 180 minutes.

As acidic catalysts can be used all soluble acids, that is to say sulphuric acid, toluenesulphonic acid, hydrochloric acid and methanesulphonic acid, and all sulphonic acid ion exchangers based on phenol-formaldehyde or on styrene-divinylbenzene, which are, for example, commercially available under the trade mark Lewatit or Dowex. Heterogeneous catalysts are used preferably. The heterogeneous catalysts are used preferably in a dry form. Moreover inorganic acidic ion exchangers such as, for example, zeolites, in particular zeolite Y and sheet silicates such as, for example, montmorillonite are also suitable. The $pK_A$ value of the acidic substances in glacial acetic acid should be less than 0, preferably less than −2.

The working-up of the reaction mixture essentially involves removal of the catalyst by filtration and removal of the excess alcohol by distillation, preferably under a vacuum.

A thin-film evaporator is preferably used for filtering off the excess alcohol. If a vacuum is created for the distillation, it is between 0.1 and 100 mbar, preferably between 0.5 and 50 mbar, particularly preferably between 1 and 10 mbar.

Continuous and batch-operated boilers and the so-called countercurrent towers are suitable for use as reactors for carrying out the synthesis. In principle all the well-known reactor systems for the reaction of liquid substances can be employed.

Chloroethylglucopyranose can be employed for various purposes, for example, for rendering polymers hydrophilic.

The small quantities of catalyst, the short reaction time and the relatively slight discoloration of the product at a high conversion of glucose constitute the particular advantage of the new method.

EXAMPLE 1

1.8 kg (10 mol) of glucose are suspended in 3.6 kg (45 mol) of chloroethanol and rapidly heated to 110° C. with stirring. The entire quantity of sugar passes into solution in less than 40 minutes.

The temperature of the reaction mixture is lowered to 80° C. by distilling off a chloroethanol-$H_2O$ mixture; to this end the pressure in the apparatus is gradually reduced.

The apparatus is aerated with nitrogen and 90 g of dry Lewatit SC 102 (ion exchanger based on sulphonated polystyrene cross-linked with divinylbenzene) is added.

30 minutes after addition of the catalyst, the gas chromatogram of a silylated sample indicates approximately 9.8% of glucose and 88.6% of chloroethyl-glucopyranose; after 90 minutes the proportions indicated are approximately 5.7% of glucose and 92.5% of chloroethyl-glucopyranose.

The reaction solution is colourless to pale yellow.

Comparative Example 180 g (1 mol) of glucose, 9 g of Lewatit SC 102 and 360 g (4.5 mol) of chloroethanol are stirred to form a suspension and heated to 80° C.

After 6 hours, gas chromatographic analysis shows that the yellow mixture still contains 25% of unreacted glucose.

We claim:

1. A method for preparing chloroethylglucopyranose comprising a) reacting glucose with from 2 to 10 times the molar amount of chloroethanol at from 100° to 130° C. in the absence of a catalyst, optionally removing water, b) further reacting the product of step (a) at 60° to 90° C. in the presence of an acidic catalyst for from 10 to 600 minutes and c) separating therefrom the chloroethylglucopyranose.

2. The method of claim 1, wherein in step (c) the catalyst is removed from the product of step (b) by filtration and the excess chloroethanol is removed under vacuum.

3. The method of claim 2, wherein the final vacuum is from 0.1 to 100 mbar.

4. The method of claim 1, wherein in the separation is effected with a thin-film evaporator.

5. The method of claim 1, wherein step (b) the acidic catalyst is an ion exchanger.

* * * * *